United States Patent [19]

Carson et al.

[11] Patent Number: 5,120,414
[45] Date of Patent: Jun. 9, 1992

[54] METHOD AND APPARATUS FOR EFFECTING CAPILLARY SAMPLE INJECTION INTO ELECTROPHORESIS APPARATUS

[75] Inventors: William W. Carson, Hopkinton; Yung-Fong Cheng, Milford, both of Mass.

[73] Assignee: Millipore Corporation, Bedford, Mass.

[21] Appl. No.: 575,251

[22] Filed: Aug. 30, 1990

[51] Int. Cl.$^5$ .............. B01D 57/02; B01D 61/42; C25B 7/00; C25D 13/00
[52] U.S. Cl. .................. 204/180.1; 204/299 R; 204/182.3
[58] Field of Search ............. 204/182.8, 299 R, 180.1

[56] References Cited

U.S. PATENT DOCUMENTS

| | | | |
|---|---|---|---|
| 4,622,124 | 11/1986 | Krusher | 204/182.8 |
| 4,631,120 | 12/1986 | Pohl | 204/182.8 |
| 4,631,122 | 12/1986 | Pohl | 204/182.8 |
| 4,859,301 | 8/1989 | Brenner | 204/299 R |
| 4,936,974 | 6/1990 | Rose | 204/299 R |

Primary Examiner—John Niebling
Assistant Examiner—Caroline Koestner
Attorney, Agent, or Firm—Andrew T. Karnakis; Paul J. Cook

[57] ABSTRACT

An electrode structure is provided for feeding a solute sample to a capillary electrophoresis separation process. The apparatus comprises a conductive plate connected to an electrical lead and an absorbent layer wet with an electrolyte solution and positioned on the plate. A membrane containing a sample is positioned on the absorbent layer in contact with an entrance end of a capillary tube forming part of the separation process. The sample is fed to the entrance part by electromigration and/or electrosmosis under the influence of an electric field induced by an electrode.

11 Claims, 2 Drawing Sheets

METHOD AND APPARATUS FOR EFFECTING CAPILLARY SAMPLE INJECTION INTO ELECTROPHORESIS APPARATUS

BACKGROUND OF THE INVENTION

This invention relates to a method and apparatus for injecting sample into a capillary electrophoresis process from a membrane.

Capillary electrophoresis (CE) is an efficient analytical separation technique for analysis of minute amounts of sample. CE separations are performed in a narrow diameter capillary tube, which is filled with an electrically conductive medium termed the "carrier electrolyte." An electric field is applied between the two ends of the capillary tube, and species in the sample move from one electrode toward the other electrode at a rate which is dependent on the electrophoretic mobility of each species as well as on the rate of fluid movement in the tube. CE may be performed using gels or liquids, such as buffers, in the capillary. In one liquid mode, known as free zone electrophoresis, separations are based on differences in the free solution mobility of sample species. In another liquid mode, micelles are used to effect separations based on differences in hydrophobicity. This is known as Micellar Electrokinetic Capillary Chromatography (MECC). In capillary gel electrophoresis, an electrically conductive gel fills the capillary tube rather than the liquid electrolyte. The gel function as an anticonnective support to minimize sample band spreading. In free zone electrophoresis, a high molecular weight solute such as polyethylene oxide or hydroxymethylcellulose can be added to the solvent to provide anticonvective effects analagous to that supplied by the gel.

CE is advantageous for several reasons. These include fast separation speed, high resolution and small sample size. For example, separation speeds using CE can be 10 to 20 times faster than conventional gel electrophoresis, and no post-run staining is necessary. In part, high resolution can be obtained through the use of high voltages because of the rapid dissipation of heat by the capillary. Further, band broadening is minimized due to the narrow capillary inner diameter. In electrophoresis, the phenomenon of electroosmosis, or electroosmotic flow (EOF) occurs. This is a bulk flow of liquid which affects all of the sample molecules regardless of charge. EOF can contribute to improved resolution or separation speed in free-zone CE.

In order to achieve the high resolution that CE is capable of, it is necessary that the sample be confined to a narrow starting zone when the electrophoretic process begins. This limits the volume of sample that can be introduced into the capillary to a very small fraction of the total capillary volume. In CE, only a few nanoliters or less of the sample solution is introduced into the capillary. Injection volumes that are much larger than this volume degrade the resolution of the CE method. In capillary electrophoresis as generally practiced today, sample solutions to be analyzed are introduced from vials. The vials must contain at least a few microliters of sample solution in order that the capillary tip can be immersed in the sample solution. After sample introduction, the capillary tip is immersed in electrolyte solution and a voltage is applied across both ends of the capillary to perform the electrophoretic separation.

The disparity described above between the volume of sample required for the physical mechanism of sample introduction (at least a few microliters) and the volume actually introduced (a few nanoliters or less) is a disadvantage of current systems. Also, in some cases samples are not readily available in solution form, such as when the sample stems from a gel electrophoresis separation and exists as a spot or band on a blotting membrane.

It would be desirable to provide a means for introducing samples into a capillary electrophoresis apparatus which does not require a large sample volume. In addition, it would be desirable to provide a means for introducing sample from sample carriers other than a solvent. It would be desirable to introduce into the capillary a larger percentage of the total available sample volume than can be effected with presently available injection procedures.

SUMMARY OF THE INVENTION

The present invention provides a method and apparatus for introducing a sample from a Porous layer into the entrance end of a capillary tube of a capillary separation process. An electrode structure is provided at the entrance end of the capillary tube which comprises a porous layer, means for providing a liquid electrolyte to the porous layer, and an electrode comprising an electrically conductive layer in contact with the porous layer. A second electrode is positioned at and in electrical contact with the exit end of the capillary tube and an electrical voltage is applied between the electrode structure and the electrode at the capillary tube exit to effect migration of the sample from the membrane into the capillary tube, past a detector and out the capillary tube exit. Generally, after injection of the sample into the capillary tube, the tube entrance is moved to a position on the porous layer which is free of sample or to a vial containing electrolyte and an electrode to permit the electrophoretic process to take place by which the sample migrates through the tube. In one embodiment an electrode structure comprising an electrically conductive layer and a porous layer wet with an electrolyte solution is positioned at the capillary tube exit. In this embodiment, the sample passes out of the capillary tube and is deposited on the porous layer at the capillary tube exit.

DESCRIPTION OF SPECIFIC EMBODIMENTS

Figure 1:
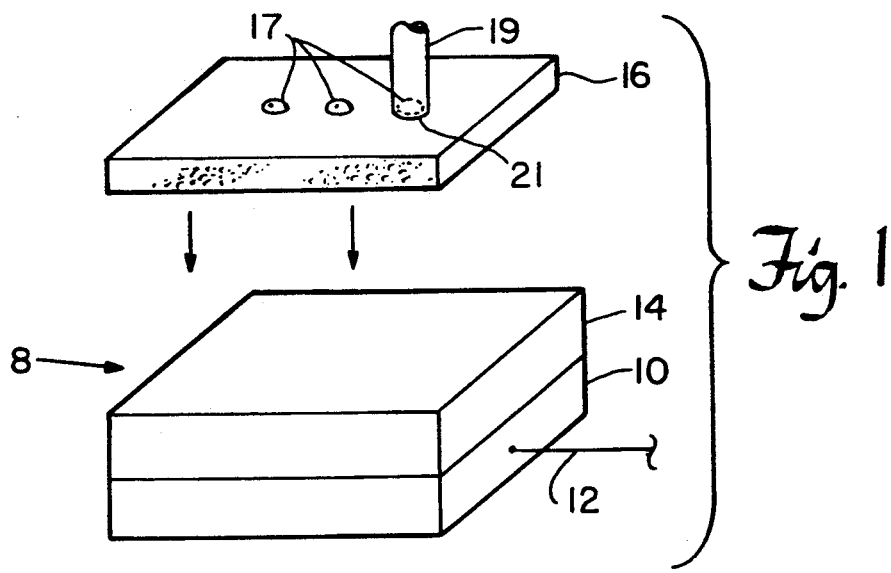
FIG. 1 is a perspective view of an electrode structure of this invention.

The term "capillary tube" as used herein means a tube having an inner diameter between about 1 and 500 micrometers.

The apparatus of this invention comprises a capillary tube having an entrance end and an exit end. Electrodes are positioned at and in electrical contact with each end of the capillary tube. Sample is introduced into the entrance end of the capillary tube from a porous layer by positioning the sample—containing porous layer on an electrode surface. The sample passes into the capillary tube by electromigration and/or electroosmosis. The porous layer contains electrolyte in order to maintain electrical conductivity between the electrode adjacent the entrance end, through the porous layer and to the capillary entrance end. In one embodiment, a second porous layer is provided between the exit end of the capillary tube and the electrode adjacent the exit end. The second porous layer is adapted to retain sample passed through the capillary tube. Generally, the second electrode is immersed in an electrolyte while the exit end of the capillary tube also is immersed in the electrolyte.

The porous layer containing a deposited sample can be positioned in contact with a wet absorbent layer under conditions to wet the porous layer. The electrolyte solution in the absorbent layer maintains electrical conductivity and wetness of the porous layer and provides overall electrical conductivity between the electrode structure and the entrance end of the capillary. Representative suitable absorbent layers include filter paper, hydrophilic membranes, fiber glass, woven fabric or the like.

The porous layer is a microporous or ultrafiltration membrane or an electrically conductive gel composition capable of retaining the sample and preventing its migration into the absorbent layer. The porous layer can comprise a hydrophilic or hydrophobic membrane or a gel such as a polyacrylamide or agarose gel. It can be advantageous to utilize a membrane which is hydrophobic when it is dry and which can be wet to become capable of transporting liquid through its thickness since these membranes can retain molecules such as proteins. Generally, when utilizing aqueous electrolytes these membranes can be wet by contacting the membrane with a water miscible organic solvent such as ethanol, methanol, acetone, acetonitrile or the like and subsequently contacting the wet membrane with an aqueous liquid. Hydrophilic membranes which can also retain proteins include polyamides and nitrocellulose. Representative membranes include those formed from polyolefins such as polyethylene, polypropylene, polymethylpentene, or the like; polystyrene or substituted polystyrenes; fluorinated polymers including poly(tetrafluoroethylene), polyvinylidene fluoride or the like; polysulfones such as polysulfone, polyethersulfone or the like; polyesters including polyethylene terephthalate, polybutylene terephthalate or the like polyacrylates and polycarbonates; polyamides, nitrocellulose, vinyl polymers such as poly vinyl chloride and polyacrylonitriles. Copolymers also can be employed such as copolymers of butadiene and styrene, fluorinated ethylene-propylene copolymer, ethylene-chlorotrifluoroethylene copolymer or the like. Generally, the microporous membrane has an average pore size between about 0.001 and 10 microns and more usually between about 0.1 and 5.0 microns. Ultrafiltration membranes comprise a membrane having a relatively open porous substructure and thin skin having small pores as is well known in the art.

The conductive layer can be solid or porous such as a screen formed from a metal, conductive graphite or carbon or the like.

Referring to FIG. 1, the electrode structure of this invention 8 comprises an electrically conductive plate 10 connected to an electrical lead 12, and a liquid absorbent layer 14. The absorbent layer 14 is applied to the plate 10 by any conventional means. The absorbent layer 14 is wet with a liquid containing an electrolyte. The porous layer 16 containing the samples 17 is positioned on the wet absorbent layer 14. The samples 17 can be contacted by the entrance end 21 of capillary 19.

Figure 2:
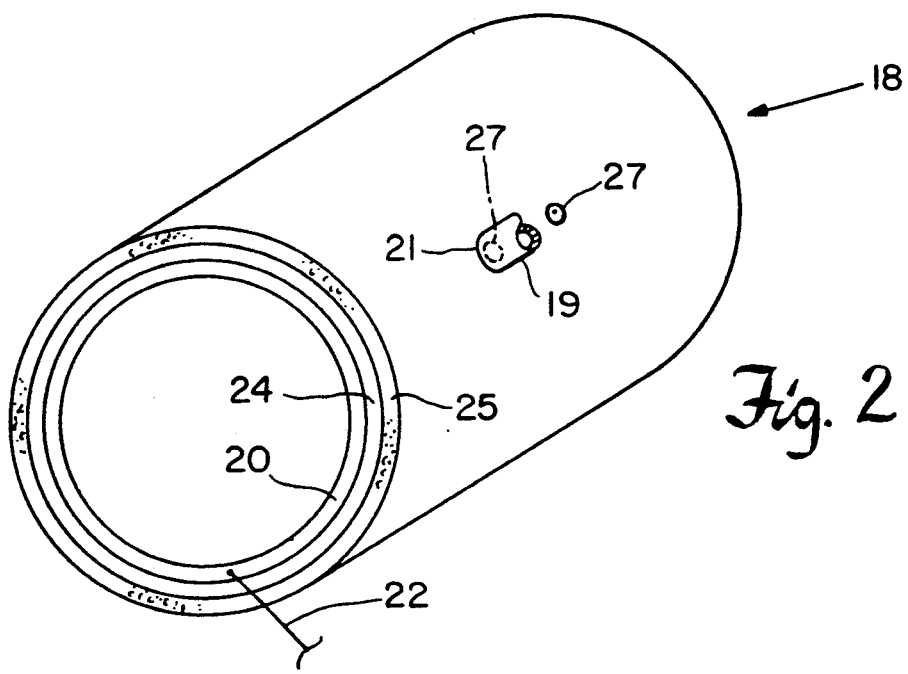
FIG. 2 is a perspective view of an alternative electrode structure of this invention.

Referring to FIG. 2, the electrode structure 18 can be in the form of a cylinder and comprises a solid or hollow cylindrical electrically conductive plate 20 connected to electrical lead 22 an absorbent layer 24. The porous layer 25 contains samples 27 can be contacted with the entrance end 21 of capillary 19.

Figure 3:
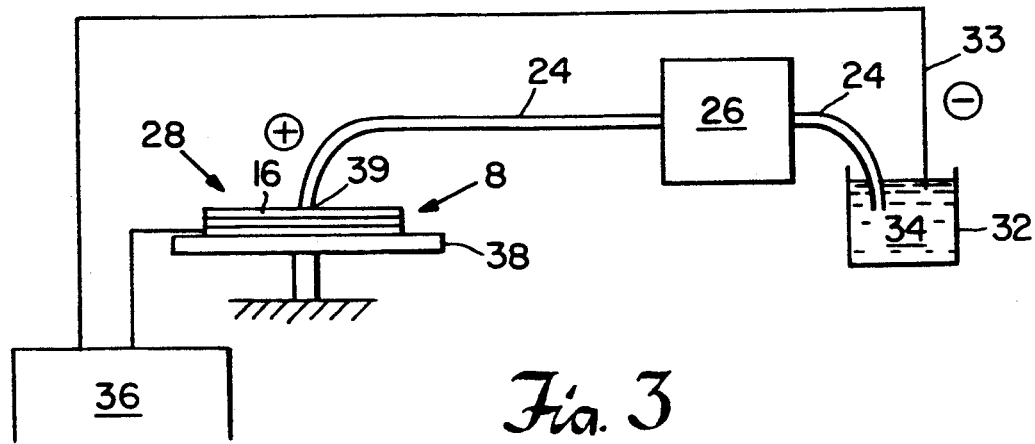
FIG. 3 is a schematic view of a capillary electrophoresis process utilizing this invention.

Referring to FIG. 3, a basic system that can be used in free zone capillary electrophoresis, capillary gel electrophoresis or micellar electrokinetic capillary chromatography is shown. As shown in FIG. 3 a capillary tube 24 which extends through detector 26 is positioned between a sample source 28 comprising the electrode structure of this invention 8 and a membrane 16 containing a sample (see FIG. 1) and a reservoir 32 containing an electrolyte 34 and electrode 33. A voltage from power supply 36 is applied between electrode 33 and electrode structure 8 while support 38 is moved under controlled conditions to present one or a plurality of samples in sequence to the entrance end 39 of capillary 24. The sample passes through the capillary tube 24, past detector 26 and into the reservoir 32. The flat electrode structure of FIG. 1 can be replaced with the cylindrical structure of FIG. 2 in which case, the cylindrical structure is rotated and/or translated axially in contact with the entrance end of the capillary tube 24.

Figure 4:
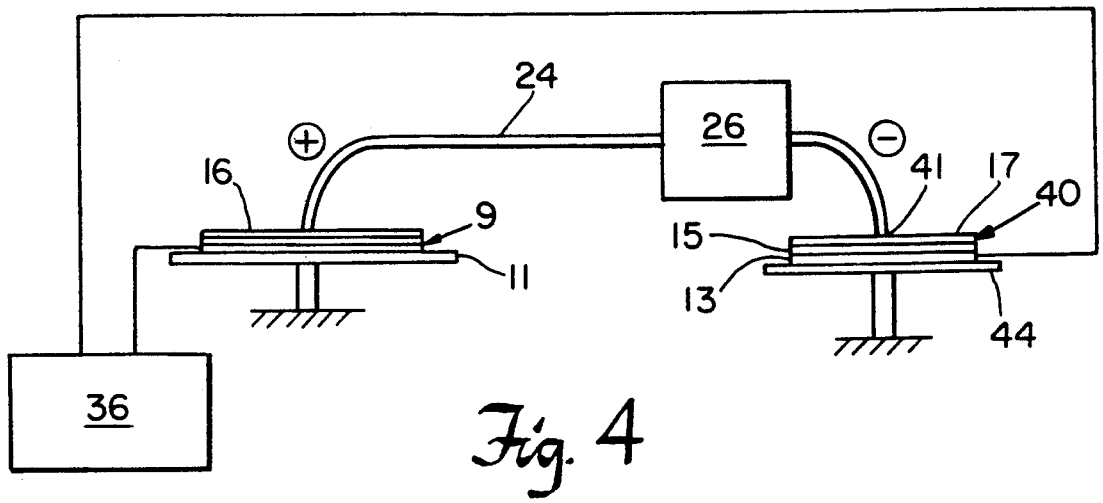
FIG. 4 is a schematic view of an alternative capillary electrophoresis process utilizing this invention.

Referring to FIG. 4 where like reference numbers in FIG. 4 refer to the same elements shown in FIGS. 1 and 3, an apparatus is shown for introducing a sample into a CE apparatus and for recovering the sample on a membrane. Membrane 16 containing a sample and wet with an aqueous liquid containing electrolyte is positioned on a conductive layer 9 positioned on support 11. The capillary tube 24 which extends through detector 26 is filled with the appropriate capillary separation composition for the capillary processes set forth above. A composite electrode structure 40 is positioned at the exit end 41. The composite electrode 40 comprises the combination of a membrane 17 on a conductive layer 13 and an absorbent layer 15 which is wet with an electrolyte solution. The sample molecules exiting from the exit end 41 of capillary tube 24 are retained by the membrane 17. The membrane 17 and associated electrode structure is positioned on support 44 which is movable so that the resolution of the electrophoretically separated samples can be retained as spatial resolution on membrane 17.

Figure 5:
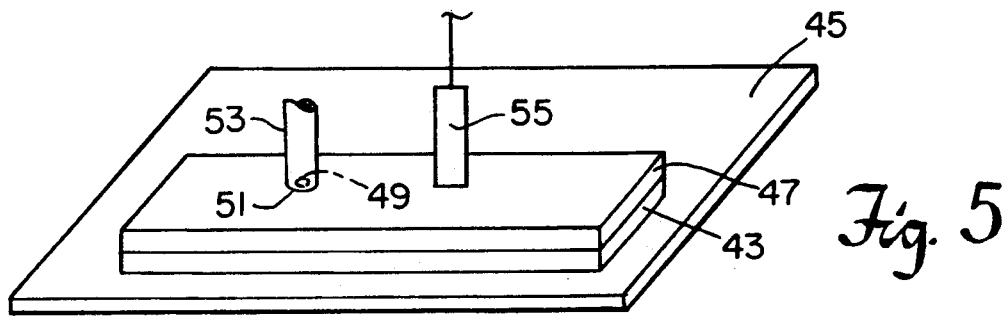
FIG. 5 shows an alternative electrode-capillary arrangement of this invention.

Referring to FIG. 5, an absorbent layer 43 containing an electrolyte is positioned on support 45. A membrane 47, wet with electrolyte and having a sample 49 retained thereon is positioned on absorbent layer 43. The entrance end 51 of capillary 53 is positioned over sample 49 and electrode 55 is contacted with membrane 47 and energized.

The following example illustrates the present invention and is not intended to limit the same.

EXAMPLE 1

This example was conducted with the apparatus of FIG. 3 utilizing CE. Experiments were performed using hydrophilic membrane (Millipore HATF 04700) as the sample substrate for sample introduction.

Figure 6:
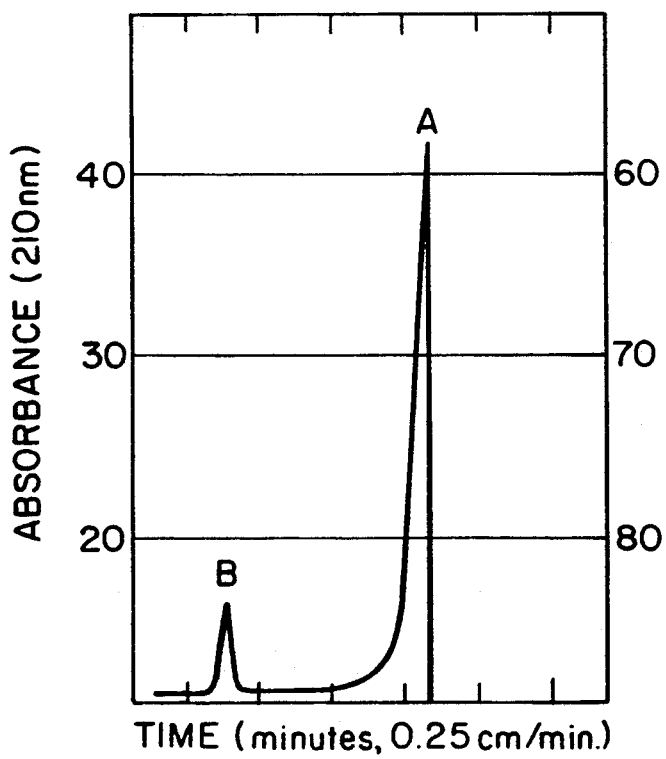
FIG. 6 shows an electropherogram of a sample introduced by the process of Example 1.

The experimental conditions were: injection time (10 sec), applied voltage (4KV), electrophoretic separation voltage (8KV), and sample solution of which 2 microliters were applied as a spot on the membrane (Cytochrome C, 38 mg/ml; Formamide, 9.1% voL/voL) UV absorbance detection at 210 nm. FIG. 6 shows the electrophoretic separation of the two components of the sample mixture after introduction into the capillary tube from the membrane. Peak A is cytochrome C, peak B is formamide.

We claim:

1. Apparatus for injecting a sample into a capillary tube which comprises:
   a. a capillary tube having an entrance end and an exit end,
   b. said capillary containing an electrically conductive composition adapted to permit sample passage therethrough,
   c. a first electrode adjacent said exit end and being in electrical contact with said electrically conductive composition within said capillary,
   d. said entrance end being in contact with a porous layer having a sample solute retained thereon,
   e. said porous layer containing a liquid electrolyte,
   f. a second electrode being in electrical contact with said porous layer, and
   g. means for effecting an electrical voltage between said first electrode and said second electrode.

2. The apparatus of claim 1 wherein said porous layer is a microporous membrane.

3. The apparatus of claim 1 wherein said porous layer is an ultrafiltration membrane.

4. The apparatus of claim 1 wherein said porous layer is a gel.

5. The apparatus of any one of claims 1, 2, 3 or 4 wherein said second electrode is a solid metal layer.

6. The apparatus of any one of claims 1, 2, 3 or 4 wherein said second electrode is a metal screen.

7. The apparatus of any one of claims 1, 2, 3 or 4 wherein an absorbent layer wetted with an electrolyte is in contact with said porous layer.

8. The process for effecting capillary electrophoresis which comprises; contacting a solute sample retained on a porous layer with an entrance end of a capillary tube containing an electrically conductive composition, said tube having said entrance end and an exit end, applying an electrical voltage between a first electrode adjacent said exit end and a second electrode adjacent said entrance end and through said electrically conductive composition, passing said solute sample through said capillary tube under the influence of electrical voltage, detecting said solute sample within said capillary tube, and depositing said solute sample on a second porous layer adjacent said exit end, said second porous layer being in electrical contract with said first electrode adjacent said exit end.

9. The process for effecting capillary electrophoresis which comprises; contacting a solute sample retained on a porous layer with an entrance end of a capillary tube containing an electrically conductive composition, said tube having said entrance end and an exit end, applying an electrical voltage between a first electrode adjacent said exit end and a second solid electrode adjacent said entrance end and through said electrically conductive composition, passing said solute sample through said capillary tube under the influence of electrical voltage, and detecting said solute sample within said capillary tube.

10. The apparatus of any one of claims 1, 2, 3 or 4 wherein said electrically conductive composition is a liquid.

11. The process of any one of claims 8 or 9 wherein said electrically conductive composition is a liquid.

* * * * *

UNITED STATES PATENT AND TRADEMARK OFFICE
CERTIFICATE OF CORRECTION

PATENT NO. : 5,120,414

DATED : June 9, 1992

INVENTOR(S) : William W. Carson and Yung-Fong Cheng

It is certified that error appears in the above—identified patent and that said Letters Patent is hereby corrected as shown below:

On the Title page,
Item [75], Inventors: add -Martin Fuchs, Uxbridge, Mass.-

Signed and Sealed this

Seventeenth Day of August, 1993

Attest:

BRUCE LEHMAN

Attesting Officer     Commissioner of Patents and Trademarks